United States Patent [19]
Harty

[11] Patent Number: 5,568,817
[45] Date of Patent: Oct. 29, 1996

[54] COMPACT DEVICE FOR CONTROLLING RUNOFF OF FLUID

[76] Inventor: Robert D. Harty, 11416 S. Homan, Chicago, Ill. 60655

[21] Appl. No.: 456,191

[22] Filed: May 31, 1995

[51] Int. Cl.$^6$ .................................................. A61B 19/00
[52] U.S. Cl. ............................ 128/849; 128/853; 4/458
[58] Field of Search .................................. 128/849–856, 128/845, 846; 4/458

[56] References Cited

U.S. PATENT DOCUMENTS

| | | | |
|---|---|---|---|
| 3,921,627 | 11/1975 | Wilson | 128/853 |
| 4,890,628 | 1/1990 | Jackson | 128/853 |
| 5,107,859 | 4/1992 | Alcorn | 128/853 |
| 5,143,091 | 9/1992 | Patnode | 128/853 |
| 5,161,544 | 11/1992 | Morris | 128/853 |

*Primary Examiner*—Michael A. Brown
*Attorney, Agent, or Firm*—Cherskov & Flaynik

[57] ABSTRACT

A disposable or semi-disposable compact device for confining runoff of hazardous fluid is provided, comprising a removably attached fluid impermeable liner form-fitted to a frame so as to conform the liner to a predetermined container shape to allow for patient decontamination or retention of fluids from leaking structures. The liner could be reused or disposed with or without the fluid.

19 Claims, 2 Drawing Sheets

COMPACT DEVICE FOR CONTROLLING RUNOFF OF FLUID

BACKGROUND OF THE INVENTION

1. Field of the Invention

This invention relates to a device for controlling runoff of fluid, and more specifically this invention relates to a device to be used in a triage setting to rapidly contain runoff from contaminated persons, ruptured containment vessels, and fluid transport vehicles.

2. Background of the Invention

The bane of existence for every fire fighter, hazardous materials response worker, and paramedic is doing a thorough job in emergency situations while minimizing risk of self exposure. A significant danger in triage situations is exposure to hazardous materials such as solvents, bloodborne pathogens, spilled fuel, contaminated water and the like.

A myriad of devices exist on the market for use in decontaminating persons contaminated with hazardous materials (e.g., U.S. Pat. No. 4,960,136), whereby the decontamination procedures use high volumes of water to dilute and wash away the hazardous substances from a patient's body surfaces. But, many of these devices are not equipped to confine full-strength fluids that are highly polar or nonpolar, or that contain high concentrations of hazardous materials. Furthermore, some of these devices incorporate relatively flimsy foundation materials, rendering said devices unusable after first use, even for such "light" service as patient decontamination and transport.

Separately, no disposable or semi-disposable device exists to handle fluid run-off from both contaminated persons and large fluid volume situations, such as leaking fuel tanks, without the danger of leakage due to overflow, device structural failure, or side-wall blow out.

Lastly, the devices now available require relatively lengthy set-up times prior to use.

A need exists in the art for a multi-utility, compact containment device that can be rapidly deployed in a matter of seconds by one worker. The device would be used to contain spilling materials, to facilitate the collection, identification and containment of cadavers or body-parts and fluids during mass casualty situations, or to rapidly contain fluid run-off during the decontamination and treatment of contaminated persons. Such a device would be at least semi-disposable to maximize protection against exposure, and also semi-permanent to minimize capital outlays for such a device.

SUMMARY OF THE INVENTION

It is an object of the present invention to provide a fluid containment device that overcomes all of the disadvantages of the prior art.

It is another object of the present invention to provide a compact fluid containment device that is disposable or semi-disposable. A feature of the device is its stowage in a rolled or flat configuration. An advantage of the device is its portability in confined space scenarios, such as on ambulances and other emergency response vehicles, and its one-person rapid deployment characteristic in triage settings. Another advantage of the device is its use as a portable autopsy table, and as a disposable unit in mass casualty situations where identification and containment of cadavers and body parts is problematic.

Another object of the present invention is to provide a decontamination device for use in treating contaminated persons. A feature of the device is the incorporation of a reusable frame and a disposable liner and absorbing material. An advantage of the invention is its utility in minimizing exposure of triage personnel to such hazardous materials as body fluids, chemicals and radiation, particularly during the bustle of containment operations and also during final disposition of the liner, while simultaneously providing cost savings with the incorporation of a reusable frame.

Yet another object of the present invention is to provide a compact fluid containment device that can be deployed in seconds by one operator. A feature of the device is its frame being constructed with durable yet flexible substrate. An advantage of the device is its rapid deployment in tank rupture scenarios wherein many gallons of fluid must be contained immediately without a danger of side or bottom blow-out to the device.

Briefly, the invention provides for a compact device for confining runoff of hazardous fluid comprising a fluid impermeable liner, a frame adapted to receive said liner so as to conform the liner to a predetermined container shape, the container shape adapted to receive fluid, a means for isolating the removal of the fluid from the container, and a means for removing the liner from the frame after use.

BRIEF DESCRIPTION OF THE DRAWING

These and other objects and advantages of the present invention will become readily apparent upon consideration of the following detailed description and attached drawing, wherein.

DETAILED DESCRIPTION OF THE INVENTION

Figure 1:
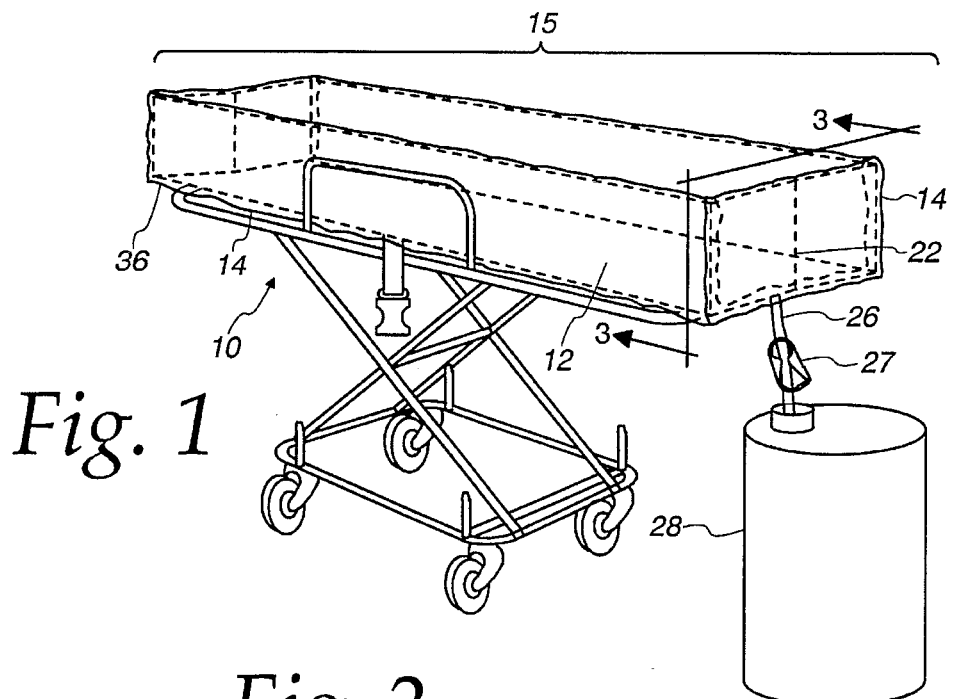
FIG. 1 is a front perspective view of an exemplary device placed upon a patient carrier, in accordance with the features of the present invention.

A myriad of different embodiments and uses of the invention are described. One exemplary embodiment of the invented device is depicted in FIG. 1 as numeral 10 whereby the device is shown positioned on a patient carrier, such as an ambulance stretcher or medical facility gurney.

Generally, the device 10 consists of a flexible yet durable frame 12 which can be compactly stored in a flat or rolled configuration. The frame is adapted to receive a liquid impermeable liner 14 which can be either reused or disposed of after use. The liner 14 is configured to be removably form fitted (analogous to a slip-cover) over the frame 12 so as to define a means for containing fluid, such as a container 15 or basin to accommodate a supine or prone person.

Alternatively, the frame 12 is constructed to enable the resulting container 15 or basin to be positioned under a tank, hopper or vehicle to receive fluid run-off from leaking structures, such as punctured fuel tanks, oil pans, transport tank trailers, or railroad tank transports.

While any object, person, or fluid placed in the device actually contacts the inside bottom surface 13 of the liner 14, the weight of the object, person or fluid is supported by the weight bearing surface that the device is setting upon, with the device 10 contacting the bearing surface via a liner contact surface 17, which is the outside bottom surface of the liner 14. Such a weight bearing surface can be, but is not limited to, a patient carrier, a platform, the ground, or any such generally flat surface.

In any of the triage applications described infra, the fully assembled device can be quickly deployed by either rolling out the device from one end, or deploying the flat-stored device simply by applying a lateral force to the opposing longitudinal side members of the device. The resulting structure is a container, generally square or rectangular in configuration, that is adapted to receive a patient directly, or on a back board or stokes basket. General dimensions of the device for patient-treatment scenarios is approximately 80 inches long, 20 inches wide, and 8 inches high.

The device 10 is ideal for triage instances and mass disaster scenarios whereby cadavers and body parts need to be collected and tagged, while simultaneously affording a means to fully view the remains. Unlike conventional morgue- or body-bags, the mouth of the container 15 remains open for such cataloging by pathologists and other morgue personnel. To facilitate closure of any contents collected in the liner, the outside edge 36 of the liner 14 is configured with Vel-Cro® type or Zip-Loc® type fasteners 38. After use, a user inverts the liner by pulling up on all of the depending liner edges 36 and then melding opposing outside edges 36 to each other via the fasteners 38 to form a pod-like structure capturing the container contents, the contents and liner 14 to be subsequently either reexamined or disposed of pursuant to OSHA or EPA regulations.

Figure 5:
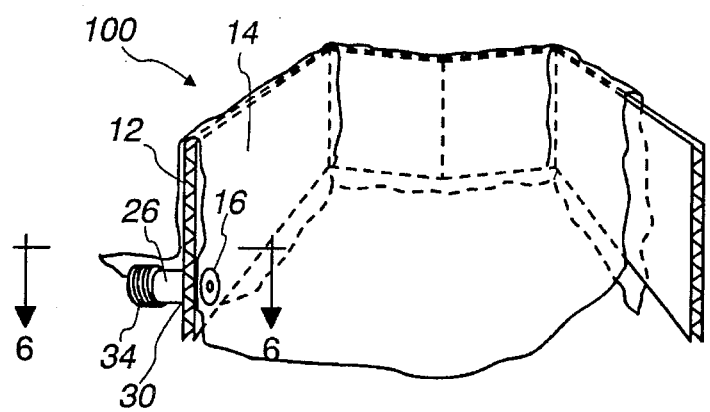
FIG. 5 is an elevated cut-away view of another exemplary device, in accordance with the features of the present invention.

The device is also configured to be placed under a leaking structure. General dimensions for a fluid retention device, partially depicted in FIG. 5 as numeral 100, will vary, and can range from 20 to 80 inches long, 20 to 80 inches wide, and 8 to 24 inches high.

The device 10 can incorporate additional means for enabling the device to be removably carried securely by a patient carrier such as an ambulance stretcher, a hospital gurney, medical exam table, autopsy table, veterinary table and the like. Such a device includes, but is not limited to, a downward extension, or a depending configuration, of longitudinal peripheral sides 18 and lateral peripheral sides 20 of the frame 12 of the device so as to form a skirt around the periphery of the patient carrier. This skirt could serve to minimize lateral- or axial-sliding on a surface of the patient carrier during transport or treatment.

Another means for enabling the device to be removably carried securely by a patient carrier is the use of an attachment means. Such attachment means includes, but is not limited to a hook-pile arrangement, such as Velcro® fasteners, whereby a contact surface 17 of the liner 14 contains an attachment site (i.e., a male coupler) that is complimentary with an attachment site (i.e., a female coupler) located on the bearing surface of a patient carrier.

Another type of attachment means includes a strap or a plurality of straps the straps employed either separately or in tandem. When the straps are supplied in pairs, a first strap 24 of the pair would have a first end attached to a bottom edge 19 of a first longitudinal peripheral side 18 or a first lateral peripheral side 20 and a second end terminating with a female coupling. A second strap 25 of the pair would have a first end attached to the bottom edge 19 of a second longitudinal peripheral side 18 or a second lateral peripheral side 20, said second side opposing the first side to which the first strap is attached. The second end of the second strap would have a complimentary surface or latch, such as a male coupler, adapted to be received by the female coupling of the first strap.

When using the straps to secure the device to a patient carrier, the coupling ends of the straps would be adapted to be mated underneath the patient resting surface of the patient carrier, in a configuration analogous to that depicted in the device disclosed in Applicant's patent application, Ser. No. 08/223,102, incorporated herein by reference. A myriad of coupling devices are acceptable, including, but not limited to, velcro-type fasteners, seat-belt type couplers, snap fit assemblies, buckle-through-strap arrangements, or the simple tying together of the loose, free ends of the straps.

When using straps to maintain the container's configuration in high fluid volume retention scenarios, such as the retention of leaking fuel from punctured or fractured automotive fuel tanks, the straps are attached to the frame in a fashion similar to that described supra, but would mated or coupled together over the top of the opening of the container 15 so as to prevent side blow-out.

If only one strap is used, a first end of the strap is attached to the unit, as described supra, and the other end is removably attached to the bottom edge of an opposing frame side. This removable attachment configuration is the type noted supra, namely snap-fit, male-female, hoop-pile, and the like.

Fluid Removal Means Detail

Depending on the anticipated use of the device, one region of the liner 14 will incorporate a means for providing fluid communication between the inside of the container 15 and the outside of the container. For example, a region of the liner may have portions defining a hole, groove, aperture 16 or the like to which is attached a means for providing fluid passage, such as a gutter, pipe or conduit 26, from the inside of the container 15 to a catch basin 28. In situations wherein a supine patient is being decontaminated, the aperture 16 is situated adjacent to the periphery of the container 15 and through the floor of the liner so as to facilitate fluid removal at one end of the container 15. The inventor has found that superior and rapid evacuation of fluid occurs when the drain means 16 is formed in a medial region of the inside bottom surface 13 of the liner 14 and adjacent to the intersection of two planes of the liner; the first plane defined by the inside bottom surface 13 and the second plane defined by an inside lateral wall surface 11 of the liner 14.

The attachment of the conduit 26 to the liner can be effected via a myriad of attachment means, including, but not limited, to RF welding, adhesive, thermal treatment, or other methods of integrally molding the conduit to the liner. Alternatively, the conduit 26 can be attached to the liner 14 via a conduit-liner-interface coupling 32, the coupling itself integrally molded with the liner.

A myriad of patient carriers are accommodated by the device with this type of drain assembly, including, but not limited to, an ambulance stretcher, hospital gurney, medical exam table, autopsy table, veterinary table, and the like.

Figure 6:
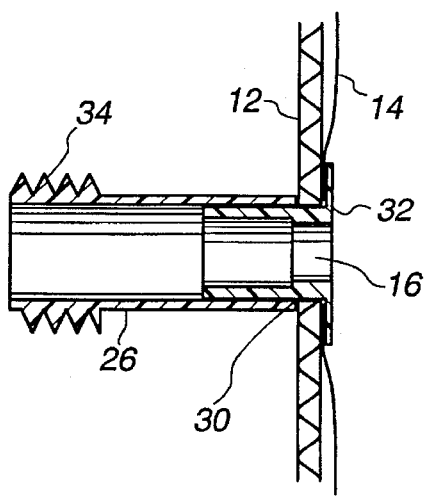
FIG. 6 is a view of FIG. 5 taken along line 6—6.

An alternative drain assembly is used in situations where large quantities of fuel or other hazardous fluids are to be confined. In one exemplary device, partially depicted in a cutaway illustration as numeral 100 in FIG. 5 and FIG. 6, the liner aperture 16 communicates with a region of the frame 12 defining a door, hole, groove, aperture, 30, or the like, through which is passed a means for providing fluid passage, such as a conduit, 26, from the inside of the container 15 to a holding area (not shown). The liner aperture 16 is juxtaposed medially and immediately adjacent to the similar size frame aperture 30 so as to render support for the entire drain assembly when the assembly is mated with a fluid evacuation means (not shown). Such a mating is accomplished by configuring the distal end 34 of the conduit means 26 as a threaded nipple (shown) to which is mated a female threaded coupling. Alternatively the distal end 34 could be formed with a female threaded coupling, the coupling adapted to receive a male threaded end. A myriad of threaded arrangements provide good results, including the standard three quarter inch threaded conduit configurations found on typical garden hoses. National Pipe Thread (NPT) gauge is a widely used thread pitch that provides good results. Other mating configurations include snap-fit assemblies and hose-clamp arrangements.

The side drain configuration, described supra, is employed in large fluid volume retention scenarios where the device is resting on the ground or on a flat, transportable or stationary surface, so as to facilitate removal of the fluid from the device prior to reclamation or disposal of the liner 14 or device 100. The removal of fluid is effected by a myriad of removal means, including siphon configurations, vacuum systems, electromechanical devices such as drain pumps, or just gravity.

The bottom drain configuration, described in patient care situations, supra, is also applicable in large fluid volume retention situations if the device is situated at one end of a platform or surface so as to allow for gravity assisted drainage.

Aside from a drain means, described supra, absorbent material, can be used to removed collected fluid from the container. Such absorbent material includes free or encapsulated particulate material, pulp, paper, cloth, polypropylene micro-fibers, or homogenous blends of the above. These materials can be encapsulated to form a suitable absorbent substrate via lamination to film, tissue, or other support substrates. Examples of such absorbent materials include Coform™ or Meltblown™ from Kimberly Clark (Rosewell, Ga.) and Chemical Sorbent™ from 3M (St. Paul, Minn.).

Figure 3:
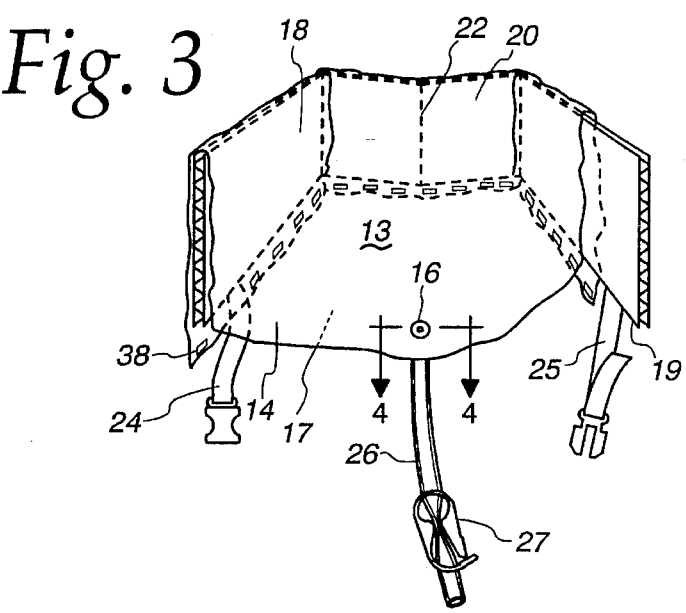
FIG. 3 is an elevated cut-away view of the device, in accordance with the features of the present invention.
Figure 4:
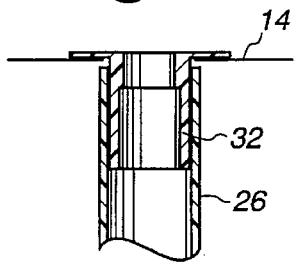
FIG. 4 is a view of FIG. 3 taken along line 4—4.

In as much as the absorbent material would often supplant the function of the conduit means 26, said means would not necessarily be used when using absorbent material. Rather, a stopping means is used to prevent fluid leakage from the liner 14 through the drain means 16. Such a stopping means is effected by a myriad of configurations, including a plug, cap or stopper adapted to be received by the conduit-liner interface coupling 32 via a friction-fit male-female configuration, or a threaded male-female, nipple-cap configuration. Alternatively in these instances, the conduit means 26 is left in place with fluid flow through the conduit means 26 stymied by a flow control means 27, said means including but not limited to a tubing control valve shown in an open position in FIG. 1 and in a closed position in FIG. 3, a needle valve, a stopcock, or a dispensing valve. These fluid control means are commercially available from domestic plastic material suppliers, including U.S. Plastic Corporation, Lima, Ohio.

Frame Detail

A salient feature of the invention is the incorporation of light weight, yet strong frame material over which the liner is fitted. A myriad of construction materials can be utilized for the frame, including, but not limited to the materials listed infra.

Figure 8:
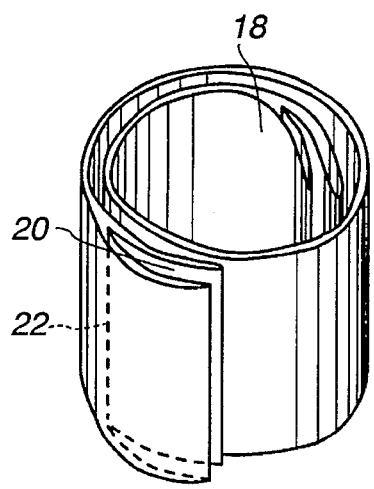
FIG. 8 is an elevated view of the frame depicted in FIG. 3, in a rolled configuration, in accordance with the features of the present invention.

The thickness of the frame fabrication material will vary, depending on anticipated use of the device. For example, if the device is to be carried in an ambulance and used primarily in medical decontamination scenarios, then a thickness ranging from between approximately 2.5 to 4.5 millimeters (ml) would be used. Good results are obtained with thicknesses of approximately 3 ml in as much as this thickness allows more compact rolling and storage of the unit prior to and after use. In addition, the rolled configuration allows for the simultaneous stowage of a small container in the opening formed by the rolled configuration. FIG. 8 depicts said rolled configuration for one exemplary frame of the device. A preferable frame material is 3 ml polypropylene Coroplast™, manufactured by Fritz Mueller A. G. 5600 Wuptertal 2 D. E. (Germany) or Cor-X™, manufactured by Woodruff Corporation, Richmond, Ind.

When the anticipated use includes containment of leaking fuel, substrates having thicknesses greater than approximately 5 ml and less than 12 ml are utilized with thicknesses selected from a range of between approximately 5 ml and 8 ml preferable.

Figure 2:
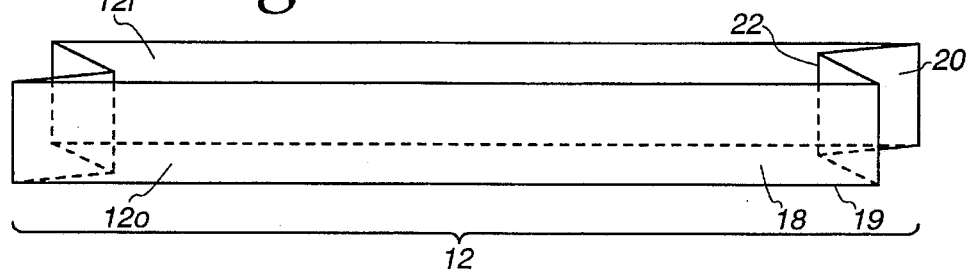
FIG. 2 is an elevational view of the frame, in a semi-deployed position, of an exemplary device, in accordance with the features of the present invention.
Figure 7:
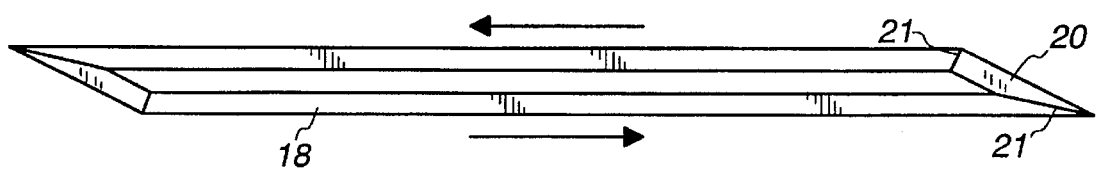
FIG. 7 is an aerial perspective view of another frame, in a semi-deployed position, of an exemplary device, in accordance with the features of the present invention.

In situations where heavier gauge substrate is required or desired, and to facilitate one-step stowage or deployment of the unit in other than a rolled configuration, the frame is constructed to allow the opposing faces of the opposite longitudinal sides to contact each other when the device is not in use. One type of stowage configuration, whereby the frame 12 is illustrated in FIG. 2 as partially deployed, is effected by a medial crease 22 in the opposed raised lateral peripheral sides 20 of the device 10. Another type of stowage configuration, illustrated in FIG. 7 as partially deployed, utilizes the folds 21 at the natural convergence points of the planes defined by the longitudinal raised peripheral sides 18 and the lateral raised peripheral sides 20 to deploy or stow the unit.

Yet another type of frame configuration is the incorporation of a single medial crease in each longitudinal side (longitudinal side crease not shown) and each lateral peripheral side so that storage and deployment of the unit is not a one-step process, described above, but rather a two-step process. First, the medial crease in the lateral peripheral sides effect close proximity to each other of the longitudinal side 18. At this point, the unit has a thickness of between 2 and 2.5 inches Then the medial crease in each longitudinal peripheral side allows the unit to fold once in a book-like fashion to effect a final thickness of approximately 4–5 inches.

The configuration of the frame allows for the device to be shipped assembled, i.e., with the liner already in place. In this manner, zero set-up time and rapid deployment in triage settings is facilitated, in either one step, or two steps. Furthermore, the slipcover designed liner 14 is easily replaced after use.

Liner Detail

Generally, liquid impermeable liners are utilized as form-fitted slip covers for the frame 12. The substrate of the liners are either flexible, semi-flexible or rigid. Liners which accommodate stowage of the device in either a folded or rolled configuration are preferable.

Liner substrates produced by standard calendering processes or film casting processes meet acceptable stability and thickness requirements. After calendering or casting, the liner is cut and RF welded to shape. An alternative shaping process is to sew the liner into a frame cover. When form-fitted to the frame, 12, the liner is designed at least to cover the inside surfaces 12i of the frame 12 and preferably also to cover the outside surfaces 12o of the frame 14 for additional support to the device 10.

Generally, liners having thicknesses ranging from between approximately 8 mils and 12 mils (1 mil= one one-thousandth of an inch) are used. Situations were the device is used to contain high fluid volumes and/or concentrated acid or alkaline liquids often require 12 mil liner thicknesses. This is also to accommodate the construction of heavy duty fluid evacuation structures of the type depicted in FIG. 6, wherein conduit nipples and mating assemblies are RF-welded, glued, heat treated or otherwise integrally molded with the liner fabric.

Another alternative to the 8 to 12 mils thicknesses for liners, as disclosed supra, are much thicker substrates, such as those used as tank liners. One such embodiment is a ⅛ inch PVC liner called Type 651, manufactured by Fabrico Tank Liner Company, of Chicago, Ill.

The liner material used in the device, 10 or 100, is impermeable to a myriad of substances, and generally withstands nonpolar fluids such as fuels, oil, and solvents, as noted infra, until such time as these fluids are evacuated from the container to a more permanent disposition. Liner materials that provide excellent containment for such fluids include the fluroplastics, polyvinyl chloride, polyurethane, polymethylpentene, high density polyethylene, and polypropylene. A more complete list of liner constituents is disclosed infra.

The liner, constructed from the materials above, also offers the ability to store polar materials fairly indefinitely. Body fluids, such as blood, semen, urine, feces, and wash water contaminated with pathogens (HIV, hepatitis) contained in bodily fluids are contained in the liner indefinitely with no threat of permeating through the liner to cause leaks.

Much of the device 10 is constructed with nonmetallic material. For example, the frame, 12, liquid-impervious liner 14, conduit 26, and strap members 24 are constructed with materials that will allow for easy cleaning, will not be prone to corrosion, and which will allow for patient cardio-conversion and defibrillation. Also, the construction materials are radiotranslucent for those instances where patients must be immobilized at the scene either for splinting purposes or for subsequent x-ray analysis.

Typical materials for the frame include, but are not limited to, plastic, glass, fiberglass, ceramic, sealed wood, treated cardboard, polyvinyl chloride, glass, thermoplastic, reinforced thermoplastic (such as polypropylene, polycarbonate, polybutylene, terephalate, and polyphenylene sulfide) and sheet molding compounds (such as polyester), or a combination of these materials. One such suitable material is the Cor-X™ material, disclosed supra.

As noted supra, the liquid impermeable sheeting material or liner 46 can be constructed from a myriad of flexible materials, such as blown film (ethylene-vinyl acetate, polyethylene, polyvinyl chloride), cast film (polyethylene, polypropylene, nylon, polyester, and polyvinyl chloride), treated cloth or any other sheeting material having long term chemical resistance. Examples of commercially available liquid impermeable material includes Tyvek® from I. E. Dupont, Atlanta, Ga., Saranex® from Dow-Corning of Midland, Mich., and 1400 GRNT, which is a flexible PVC film available through Wiman Corporation, St. Cloud, Minn.

Other suitable liner materials include polyallomer, polymethylpentene, and fluoroplastics such as fluorinated ethylene polypropylene, tetrafluoroethylene, perfluoroalkoxy resin, ethylenetetrafluoroethylene, and ethylene chlorotrifluoroethylene.

The liner 14, is relatively impermeable to a myriad of substances, including, but not limited to, water, various alcohols (including methanol, ethanol, propanol, isopropanol, butanol, etc.) ketones, aldehydes and other polar and nonpolar aliphatics, (substituted or otherwise, for example degreasers such as the halogenated ethylenes, carbon tetrachloride, chloroform), the most commonly transported polar and nonpolar aromatics (such as toluene, benzene, halogenated aromatics, xylene, substituted aromatics, etc.), polyaromatics (such as naphthalene and its halogenated counterparts), biphenyls (such as polyhalogenated dibenzo dioxins, pesticides, etc.), organic and inorganic acids and alkalies, various motor fuels, inorganic compounds (such as ammonia and the halogens fluorine, chlorine, bromine and iodine), among others. Obviously, permeability will not be absolute for all substances. However, the nature of the materials used to construct the device (reinforced thermoplastics, for example are extremely resilient to polar and nonpolar chemicals), and the operation of the invented device as a patient carrier (wherein copious amounts of water and surfactants are employed in decontamination procedures to dilute the contagion) result in minimal direct and sustained contact of the above enumerated compounds to the device 10 at high molarities. Therefore, in patient care scenarios, the structural integrity of the device 10 will not be compromised even when liner constituent material, which is not as chemically resistant as those listed supra, is utilized.

While the invention has been described with reference to details of the illustrated embodiment, these details are not intended to limit the scope of the invention as defined in the appended claims.

The embodiment of the invention in which an exclusive property or privilege is claimed is defined as follows:

1. A compact device for confining runoff of hazardous fluid comprising:
   a.) a fluid impermeable liner;
   b.) a frigid, reusable frame adapted to removably receive said liner so as to conform the liner into a container, said container adapted to receive the fluid;
   c.) a means for removing the fluid from the container; and
   d.) a means for removing the liner from the frame after use.

2. The device as recited in claim 1 wherein the fluid impermeable liner is flexible.

3. The device as recited in claim 1 wherein the frame has raised peripheral sides.

4. The device as recited in claim 3 wherein the raised peripheral sides define a container which can be placed underneath a motor vehicle.

5. The device as recited in claim 3 wherein the raised peripheral sides define a container adapted to receive a person contaminated by hazardous materials while allowing simultaneous full body access to the person.

6. The device as recited in claim 1 wherein the means for removing fluid is integrally molded with the liner.

7. The device as recited in claim 1 wherein the means for removing fluid is RF welded to the liner.

8. The device as recited in claim 1 wherein the device includes a means for being carried by a patient carrier.

9. The device as recited in claim 8 wherein the patient carrier is a standard hospital gurney.

10. The device as recited in claim 1 wherein the patient carrier is an ambulance stretcher.

11. The device as recited in claim 1 whereby the means for removing fluid is absorbent material.

12. A semi-disposable device for decontaminating a person contaminated with hazardous materials comprising:

a.) a liquid-impermeable liner;

b.) a rigid reusable frame adapted to removably receive said liner and to conform the liner to produce a container having a predetermined shape, said container adapted to receive the person, while allowing simultaneous full body access to the person;

c.) a means for removing fluid from the container; and d.) a means for removing the liner from the frame after use.

13. The device as recited in claim 12 wherein the liquid impermeable liner is removably attached to the frame.

14. The device as recited in claim 12 wherein the device is stowed in a rolled configuration.

15. The device as recited in claim 12 wherein the device is stowed in a folded configuration.

16. The device as recited in claim 12 wherein the means for removing the fluid is integrally molded with the liner.

17. The device as recited in claim 12 wherein the means for removing the fluid is absorbent material.

18. The device as recited in claim 12 wherein the device includes a means for being carried by a patient carrier.

19. The device as recited in claim 12 wherein the person is supine or prone.

* * * * *

UNITED STATES PATENT AND TRADEMARK OFFICE
CERTIFICATE OF CORRECTION

PATENT NO.   : 5,568,817
DATED        : October 29, 1996
INVENTOR(S)  : Robert D. Harty It is certified that error appears in the above-indentified patent and that said Letters Patent is hereby corrected as shown below:

Column 8, line 37, delete the word "frigid" and insert the word
    --rigid--.

Signed and Sealed this

Eighteenth Day of February, 1997

Attest:

BRUCE LEHMAN

*Attesting Officer*     *Commissioner of Patents and Trademarks*